(12) United States Patent
Frey

(10) Patent No.: US 7,989,514 B2
(45) Date of Patent: Aug. 2, 2011

(54) STRONG-ACID CATION EXCHANGE RESINS

(75) Inventor: Johann-Wilhelm Frey, Stade (DE)

(73) Assignee: Dow Global Technologies LLC (US)

( * ) Notice: Subject to any disclaimer, the term of this patent is extended or adjusted under 35 U.S.C. 154(b) by 392 days.

(21) Appl. No.: 12/377,013

(22) PCT Filed: Jul. 18, 2007

(86) PCT No.: PCT/US2007/016291
§ 371 (c)(1),
(2), (4) Date: Feb. 10, 2009

(87) PCT Pub. No.: WO2008/030299
PCT Pub. Date: Mar. 13, 2008

(65) Prior Publication Data
US 2011/0152389 A1    Jun. 23, 2011

Related U.S. Application Data

(60) Provisional application No. 60/842,833, filed on Sep. 7, 2006.

(51) Int. Cl.
*B01J 31/10* (2006.01)
*B01J 47/00* (2006.01)

(52) U.S. Cl. ........................................... 521/32; 521/25

(58) Field of Classification Search ............... 521/25, 521/32
See application file for complete search history.

(56) References Cited

U.S. PATENT DOCUMENTS 5,212,206 A * 5/1993 Rudolph et al. ............... 521/32
* cited by examiner

*Primary Examiner* — Michael M Bernshteyn

(57) ABSTRACT

A strong-acid cation exchange resin comprising a plurality of acid groups which are partially neutralized with a cation of formula (I); wherein $R^1$ at each occurrence independently is hydrogen or a Ci-4-alkyl group, $R^2$ at each occurrence independently is hydrogen, alkyl or aryl, $R^3$ at each occurrence independently is hydrogen or alkyl or two vicinal groups $R^3$ together form an aromatic ring, m is 1, 2, 3, 4, 5 or 6, n is 1, 2, 3 or 4, o is 1 or 2, and p is 1, 2 or 3, is useful in the production of bisphenols.

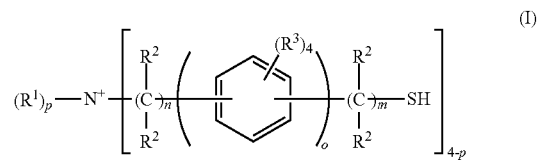

(I)

14 Claims, No Drawings

US 7,989,514 B2

STRONG-ACID CATION EXCHANGE RESINS

CROSS REFERENCE TO RELATED APPLICATIONS

This is a §371 application of PCT International Patent Application Number PCT/US2007/016291 filed Jul. 18, 2007, and claims priority from provisional application Ser. No. 60/842,833 filed Sep. 7, 2006, each of which is incorporated herein by reference in its entirety.

BACKGROUND OF THE INVENTION

The present invention relates to strong-acid cation exchange resins and to a process for producing such resins.

Strong-acid cation exchange resins and their use in the production of bisphenols are generally known in the art. U.S. Pat. No. 5,212,206 discloses a strong acid cation-exchange resin which is neutralized with a mercaptoamine in an anhydrous medium. U.S. Pat. No. 3,760,006 teaches that the modification of a strong-acid cation exchange resin in acid form by partial neutralization with a thiazolidine yields an improved catalyst for the preparation of bisphenol. U.S. Pat. No. 4,584,416 discloses partial neutralization of a sulfonated ion exchange resin by means of an N-alkylamino alkylmercaptan hydrochloride or hydrotosylate salt. U.S. Pat. No. 4,595,704 discloses that known methods for producing partially neutralized ion-exchange resins employ azirine compounds which are somewhat hazardous. The U.S. patent suggests the use of less costly and less hazardous N-(2-mercaptoalkyl)amides to prepare a strong-acid cation exchange resin which is partially neutralized with an aminoalkanethiol. U.S. Pat. No. 6,740,684 discloses a process wherein a strong-acid cation exchange resin in acid form is contacted with an alkyl carbamoyl alkyl thioester to produce a cation exchange resin wherein the acid groups are partially neutralized with a mercaptoalkylamine.

Bisphenols are prepared on very large scale, specifically bisphenol A is produced at an amount of more than a million metric tons/year. Therefore, there is a constant need to find new cation exchange resins which are useful for producing bisphenols of high selectivity. Accordingly, one object of the present invention is to provide a new cation exchange resin which is useful for producing bisphenols. A preferred object of the present invention is to provide a new cation exchange resin which is useful for producing bisphenols, particularly bisphenol A, with a selectivity that is at least as good or preferably even better than the selectivity that is achieved with the aid of known cation exchange resins.

SUMMARY OF THE INVENTION

One aspect of the present invention is a strong-acid cation exchange resin which comprises a plurality of acid groups being partially neutralized with a cation of formula I

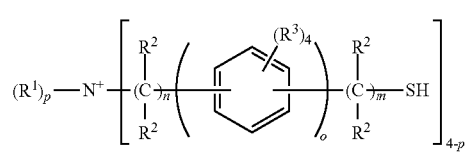

wherein
$R^1$ at each occurrence independently is hydrogen or a $C_{1-4}$-alkyl group,
$R^2$ at each occurrence independently is hydrogen, alkyl or aryl,
$R^3$ at each occurrence independently is hydrogen or alkyl or two vicinal groups $R^3$ together form an aromatic ring,
m is 1, 2, 3, 4, 5 or 6,
n is 1, 2, 3 or 4,
o is 1 or 2, and
p is 1, 2 or 3.

Another aspect of the present invention is a process for partially neutralizing a strong-acid cation exchange resin. The process comprises contacting a strong-acid ion exchange resin in acid form with a compound of formula II

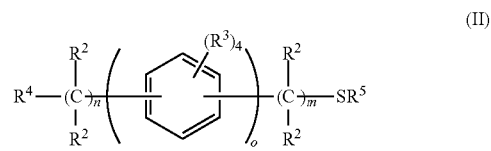

wherein
$R^2$ at each occurrence independently is hydrogen, alkyl or aryl,
$R^3$ at each occurrence independently is hydrogen or alkyl or two vicinal groups $R^3$ together form an aromatic ring,
$R^4$ is $R^6$—C(O)—NH— or $(X^{z-})_{1/z}(R^1)_p(R^8)_{3-p}N^+$—
$R^5$ is hydrogen or —C(O)—$R^7$
wherein
$R^1$ at each occurrence independently is hydrogen or a $C_{1-4}$-alkyl group,
$R^6$ and $R^7$ each independently are a $C_{1-4}$-alkyl group,
$R^8$ is a group of formula III

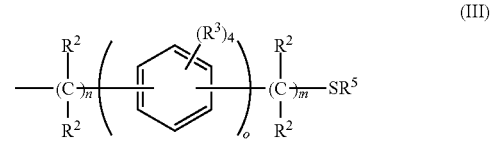

$X^{z-}$ is an anion,
n is 1, 2, 3 or 4,
m is 1, 2, 3, 4, 5 or 6,
o is 1 or 2,
p is 1, 2 or 3, and
z is 1, 2, 3 or 4.

Another aspect of the present invention is a process for producing a bisphenol wherein a phenolic compound is reacted with a carbonyl compound in the presence of the above-mentioned strong-acid cation exchange resin or in the presence of the strong-acid cation exchange resin produced according to the above-mentioned process.

Yet another aspect of the present invention is a process for isomerizing by-products resulting from the production of a bisphenol by reaction of a phenolic compound with a carbonyl compound wherein the by-products are contacted with the above-mentioned strong-acid cation exchange resin or with the strong-acid cation exchange resin produced according to the above-mentioned process.

DETAILED DESCRIPTION OF THE INVENTION

In the formula I above $R^1$ at each occurrence independently is hydrogen or a $C_{1-4}$-alkyl group, preferably methyl, ethyl or propyl. Most preferably, each group $R^1$ is methyl.

$R^2$ at each occurrence independently is hydrogen, alkyl or aryl. Alkyl groups preferably have from 1 to 6, more preferably from 1 to 4 carbon atoms, most preferably methyl, ethyl or propyl. The preferred aryl group is phenyl. Most preferably, $R^2$ at each occurrence is hydrogen.

$R^3$ at each occurrence independently is hydrogen or alkyl or two vicinal groups $R^3$ together form an aromatic ring. Alkyl groups preferably have from 1 to 6, more preferably from 1 to 4 carbon atoms, most preferably methyl, ethyl or propyl. If two vicinal groups $R^3$ together form an aromatic ring, the two vicinal groups $R^3$ together preferably have 3 or 4 carbon atoms, such that they form an aromatic 5- or 6-ring together with the carbon atoms to which they are bonded.

The meaning of m is 1, 2, 3, 4, 5 or 6, preferably 2, 3 or 4, more preferably 2; n is 1, 2, 3 or 4, preferably 1 or 2, more preferably 1; o is 1 or 2, preferably 1; and p is 1, 2 or 3, preferably 2 or 3, more preferably 3.

Strong-acid cation exchange resins are partially neutralized with the cation of formula I above. Strong-acidic cation exchange resin are known in the art, see for example "Ullmann's Encyclopedia of Industrial Chemistry", $7^{th}$ Edition, chapter "Ion Exchangers". Usually they have a polymeric matrix and functional ion exchange groups.

One known type of matrix is based on phenol/formaldehyde or benzene condensation polymers that are cross-linked with an aldehyde, a chlorinated hydrocarbon or an epoxy compound. The preferred matrixes are cross-linked polystyrene or cross-linked poly(alpha-methylstyrene) or a cross-linked polymer of styrene or alpha-methylstyrene which is substituted at the benzene ring with $C_{1-6}$-alkyl, for example methyl, ethyl, isopropyl or tert. butyl, or with halogeno-$C_{1-6}$-alkyl, such as chloromethyl, or with aminomethyl. The cross-linking agent preferably is divinylbenzene or trivinylbenzene.

Strong-acid cation exchange groups can be directly or indirectly bound to the polymeric matrix. For example, the strong-acid cation exchange groups can be bound to the polymeric matrix via alkylene groups, such as $C_{1-3}$-alkylene groups, preferably ethylene or methylene with methylene being the most preferred group. Strong-acid cation exchange groups typically are —$SO_3H$ or —$PO_3HR$ groups wherein R is hydrogen, a $C_{1-6}$-alkyl group, such as a methyl, ethyl, n-propyl, isopropyl, n-butyl, isobutyl, the pentyl or hexyl groups, a $C_{3-6}$-cycloalkyl group, such as cyclohexyl, or aryl, such as phenyl or benzyl. The most preferred strong-acid cation exchange group is —$SO_3H$. A part of the groups can be present in the salt form, for example in the alkali or alkaline earth metal salt form. However, preferably more than 95 percent, more preferably more that 99 percent, most preferably substantially all groups are in the acid form prior to partial neutralization according to the process of the present invention with a compound of formula II.

Examples of suitable strong-acid cation exchange resins include perfluorinated sulfonic acid resins, strong-acid resins prepared by phosphonation of styrene-divinylbenzene resins, sulfonated phenol-formaldehyde resins, sulfonated polystyrene resins, sulfonated styrene-divinylbenzene resins and polymers such as those disclosed in U.S. Pat. Nos. 4,303,551 and 4,330,654. The sulfonated resins are commercially available as gelular and macro-reticular types. Particularly suitable are aromatic sulfonic acid resins having a cation exchange capacity of at least 0.5 meq/g dry weight and advantageously 2.0 meq/g. Commercial strong-acid cation exchange resins prepared by the sulfonation of a styrene-divinylbenzene resin, as described, for example, in U.S. Pat. Nos. 2,597,438; 2,642,417 or 3,037,052 are most preferably used. Such commercial sulfonic acid resins are Dowex 50 resins, Amberlite IR-120 resin, Amberlite 200 resin and Duolite C20 resin which normally have an exchange capacity of from 4 to 5.5 meq/g dry weight (Dowex, Amberlite and Duolite are trademarks).

The strong-acid cation exchange resin is partially neutralized by contacting it in acid form with a compound of formula II

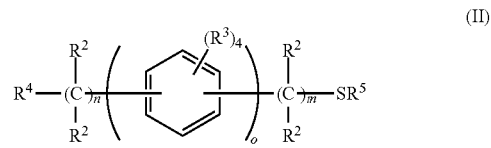

wherein
$R^4$ is $R^6$—C(O)—NH— or, preferably, $(X^{z-})_{1/z}(R^1)_p(R^8)_{3-p}N^+$—
$R^5$ is hydrogen or, preferably, —C(O)—$R^7$,
$R^6$ and $R^7$ each independently are a $C_{1-4}$-alkyl group, more preferably methyl or ethyl, most preferably methyl,
$R^8$ is a group of formula III

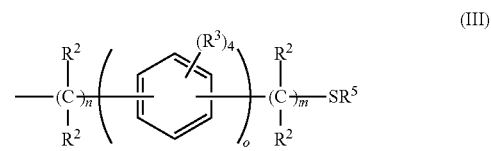

$R^1$, $R^2$, $R^3$, m, n and o have the meanings as indicated for formula I above,
$X^{z-}$ is an anion, preferably a halogenide, such as fluoride, bromide or, most preferably fluoride, or sulfate or tosylate.
p is 1, 2 or 3; preferably 2 or 3, more preferably 3, and
z is 1, 2, 3 or 4; preferably 1.

Typically about a molar equivalent of a compound of formula II is employed per equivalent of acidic ion exchange groups to be neutralized. If in the compound of formula II $R^4$ is $R^6$—C(O)—NH— and/or if the group —$SR^5$ is —S—C(O)—$R^7$, water is typically employed in an amount sufficient to hydrolyse the group $R^6$—C(O)—NH— to the group $H_2N$— and the group —S—C(O)—$R^7$ to the —SH group. The hydrolysis is substantially quantitative. Typically from 0.2 to 5, preferably from 0.5 to 3, volumes of water are employed per volume of resins beads. Water can be used alone or in combination with an organic solvent. Preferred organic solvents are ketones, such as acetone, alcohols, such as methanol or ethanol, phenols, such as phenol, or aromatic hydrocarbons, such as toluene. The reaction of an ion exchange resin with a compound of formula II wherein $R^4$ is $R^6$—C(O)—NH— leads to an ion exchange resin which is partially neutralized with a cation of formula I wherein each $R^1$ is hydrogen.

The reaction of the strong-acid ion exchange resin with the compound of formula II is preferably carried out at a temperature of from 50 to 120° C., more preferably from 80 to 110° C., most preferably at reflux temperature. The extent of neutralization of the ion exchange resin may vary widely. Typically from 5 to 60 mole percent, preferably from 10 to 40 mole percent, more preferably from 15 to 35 mole percent of the acidic groups of the cation exchange resin are neutralized. The degree of neutralization is readily verified by measuring via conventional methods, such as titration using NaOH, the ion exchange capacity of the resin before and after neutralization.

The produced partially neutralized strong-acid cation exchange resin is an effective catalyst for the preparation of many bisphenols by reaction of a phenolic compound with a carbonyl compound. The reaction of a phenolic compound with a stoichiometric excess of a carbonyl compound is known in the art. The process is described in general in U.S. Pat. Nos. 3,049,569 and 4,107,218 and in the references cited therein. The molar ratio between the phenolic compound and the carbonyl compound preferably is between 2:1 and 45:1, more preferably from 4:1 to 14:1.

Useful phenolic compounds should be unsubstituted in para position, but they can be substituted in ortho- or meta-position with one or more non-reactive groups, such as alkyl or halogen. Preferred phenolic compounds are those of formula (IV)

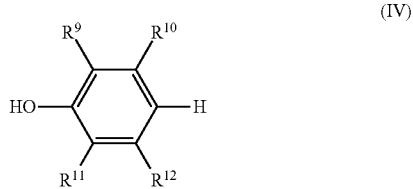

wherein $R^9$, $R^{10}$, $R^{11}$ and $R^{12}$ independently of one another represent hydrogen, halogen, preferably chlorine or bromine, or $C_{1-8}$-alkyl, preferably methyl, ethyl or tertiary butyl.

Preferred examples of the compounds of formula (IV) are phenol, mono-, di-, tri- or tetraalkylphenols, such as o-cresol or m-cresol; o-sec.butylphenol, o-tert.butylphenol, 2,6-dimethylphenol, 3,5-dimethylphenol, 2-methyl-6-tert.butylphenol, 2-isopropyl-5-methyl-phenol, 5-isopropyl-2-methyl-phenol, 2-methyl-6-ethylphenol, 2,3,6-trimethylphenol, 2,3,5,6-tetramethylphenol, 2,6-ditertiary-butylphenol, 3,5-diethylphenol or 2-methyl-3,5-diethylphenol; chlorophenols, such as o-chlorophenol or m-chlorophenol; dichlorophenols or bromophenols, such as o-bromophenol.

The carbonyl compound employed for producing the bisphenol can be a ketone or an aldehyde. Preferred carbonyl compounds are those of the following formula V

wherein
$R^{13}$ is an aliphatic, cycloaliphatic, aromatic or heterocyclic group, and
$R^{14}$ is hydrogen or an aliphatic, cycloaliphatic, aromatic or heterocyclic group or
$R^{13}$ and $R^{14}$ together represent a divalent aliphatic or aromatic group.

Preferred groups $R^{13}$ and $R^{14}$ are $C_{1-8}$-alkyl, $C_{5-6}$-cycloalkyl, $C_{5-10}$-aryl, preferably phenyl, or $C_{7-12}$-aralkyl, preferably phenyl-$C_{1-4}$-alkyl, more preferably benzyl. These groups are optionally halogenated. When $R^{13}$ and $R^{14}$ together represent a divalent aliphatic group, the group preferably is —$(R^{13}CR^{14})_q$— wherein $R^{13}$ and $R^{14}$ in each occurrence individually selectable are hydrogen or $C_{1-6}$-alkyl, such as methyl or ethyl, and q is an integer from 4 to 7, preferably 4 or 5.

Examples of suitable ketones include, for example, acetone, 1,3-dichloroacetone, methyl ethyl ketone, diethyl ketone, dibutyl ketone, methyl isobutyl ketone, cyclohexanone, fluorenone, preferably 9-fluorenone, propionylphenone, methyl amyl ketone, mesityl oxide, cyclopentanone or acetophenone. Examples of suitable aldehydes include formaldehyde, acetaldehyde, propionaldehyde, butyraldehyde and benzaldehyde. The most preferred carbonyl compound is acetone.

The phenolic compound and the carbonyl compound are preferably reacted at a temperature of from 35 to 100° C., more preferably from 40 to 90° C., most preferably from 45 to 85° C.

The strong-acid cation exchange resin modified according to the present invention is particularly useful in the production of bisphenol A from phenol and acetone. It has been surprisingly found that a higher purity of the 4,4'-dihydroxy-2,2-diphenylpropane (commonly called the p,p'-isomer of bisphenol A or simply bisphenol A) can be achieved when using the strong-acid cation exchange resin modified according to the present invention as a catalyst instead of a strong-acid cation exchange resin which has been modified with dimethylthiazolidine or 2-mercaptoethylamine hydrochloride (also designated as cysteamine hydrochloride), both of which are commonly used modifiers. When using the strong-acid cation exchange resin modified according to the present invention, the amount of the undesired by-product 2,4'-dihydroxy-2,2-diphenylpropane (commonly called the o,p'-isomer of bisphenol A) is generally only up to about 2 percent, based on the weight of the p,p'-isomer of bisphenol A. This amount is generally at least about 15 percent lower, in many cases even at least about 20 percent lower than the amount of the o,p'-isomer of bisphenol A that is obtained in the presence of a corresponding strong-acid cation exchange resin which has been modified with dimethylthiazolidine or 2-mercaptoethylamine hydrochloride. Surprisingly, it has also been found that the strong-acid cation exchange resin modified according to the present invention is active over a surprisingly long time before it has to be exchanged as a catalyst in the bisphenol production process.

Furthermore, the strong-acid cation exchange resin produced according to the present invention is useful as a catalyst for isomerizing by-products resulting from the above-described production of a bisphenol, preferably for isomerizing by-products which result from the production of bisphenol A and which include 2,4'-dihydroxy-2,2-diphenylpropane. The produced strong-acid cation exchange resin is particularly useful for isomerizing 2,4'-dihydroxy-2,2-diphenylpropane to 4,4'-dihydroxy-2,2-diphenylpropane. The isomerization process is generally known in the art.

The following examples are provided to illustrate the present invention. The examples are not intended to limit the scope of the present invention and they should not be so interpreted. Amounts are in weight parts or weight percentages unless otherwise indicated.

Example 1

Preparation of Thioacetyl-2-ethyl-[4-benzyl]-trimethyl-ammonium chloride (the compound of formula II wherein each $R^2$ and each $R^3$ are hydrogen, $R^4$ is $(X^{z-})_{1/z}(R^1)_p(R^8)_{3-p}N^+$—, $R^5$ is —C(O)—$R^7$, each $R^1$ is methyl, $R^7$ is methyl, m is 2, n is 1, o is 1, p is 3, $X^-$ is chloride and z is 1.)

52.94 g of ethenyl-[4-benzyl]-trimethyl-ammonium chloride, is dissolved in 250 ml of ethanol. Subsequently 12.5 g of azoisobutylnitrile is added. Then 19.03 g of thioacetic acid is added by a dropping funnel over 1 hour. The reaction mixture is heated up to 70 C. After cooling to 35° C. ethanol is evaporated by a vacuum of about 20 mbar.

Preparation of the Partially Neutralized Cation Exchange Resin 50 g of thioacetyl-2-ethyl-[4-benzyl]-trimethyl-ammonium chloride produced according to the above procedure, 500 ml of a wet, strong-acid cation exchange resin which comprises sulfonic acid groups and a polymer matrix of styrene cross-linked with 4 percent of divinylbenzene and 1000 ml of water are placed in a flask. The strong-acid cation exchange resin is commercially available under the trademark DOWEX 50WX4 from The Dow Chemical Company and has a cation exchange capacity of 1.2 meg/ml (5.3 meq/g). The mixture is stirred under reflux for 6 hours and then cooled to room temperature under inert conditions. The resin is filtrated and washed with acetone and water. Analysis of the resin by titration with NaOH shows that 23 percent of its acid capacity is neutralized with 2-mercapto-ethyl-[4-benzyl]-trimethyl-ammonium chloride.

Comparative Example A 4 g of 2,2-dimethylthiazolidine, 100 ml of the above-described strong-acid cation exchange resin, which is commercially available under the trademark DOWEX 50WX4 from The Dow Chemical Company, and 250 ml of water are stirred for one hour at room temperature, then filtrated and washed with another 250 ml of water. A cation exchange resin is prepared of which 25 percent of its acid capacity is neutralized with 2,2-dimethylthiazolidine.

Comparative Example B 4 g of 2-mercaptoethylamine hydrochloride (also designated as cysteamine hydrochloride), 100 ml of the above-described strong-acid cation exchange resin, which is commercially available under the trademark DOWEX 50WX4 from The Dow Chemical Company, and 250 ml of water are stirred for one hour at room temperature, then filtrated and washed with another 250 ml of water. A cation exchange resin is prepared of which 25 percent of its acid capacity is neutralized with 2-mercaptoethylamine.

Use of the Modified Catalyst

A stainless steel reactor column is charged with 500 ml of the partially neutralized cation exchange resin prepared according to Example 1 or Comparative Example A or B. The resin is dried by flushing the resin bed with twice its volume of phenol at 60° C. The catalyst is ready for use. The catalyst activity is tested by pumping a liquid consisting of phenol and acetone in a molar ratio of 10:1 at a speed of 4 ml/min. through the column containing the catalyst at 70° C. The amounts of bisphenol A (the p,p'-isomer) and of the o,p'-isomer of bisphenol A in the resulting product mixture are analysed by gas chromatography. The percent o,p'-isomer, based on the weight of the p,p'-isomer of bisphenol A and the yield of p,p'-isomer of bisphenol A, based on the weight of phenol used in the reaction, are listed in Table 1 below.

TABLE 1

| (Comparative) Example | cation exchange resin partially neutralized with | Percent Neutralization | Yield p,p'-isomer (%) | Percent o,p'-isomer |
|---|---|---|---|---|
| 1 | 2-mercapto-ethyl-[4-benzyl]-trimethyl-ammonium chloride | 23 | 96.3 | 1.9 |
| A | Dimethylthiazolidine | 25 | 95.8 | 2.5 |
| B | 2-mercaptoethylamine hydrochloride | 25 | 95.8 | 2.5 |

The lower percentage of o,p'-isomer and the higher yield of p,p'-isomer means that a more pure product at a higher yield is obtained according to Example 1, as compared to Comparative Examples A and B. The small difference in neutralization of the acid groups (23 percent in Example 1 but 25 percent in Comparative Examples A and B) does not influence the percentage of o,p'-isomer.

The invention claimed is:

1. A strong-acid cation exchange resin comprising a plurality of acid groups being partially neutralized with a cation of formula I

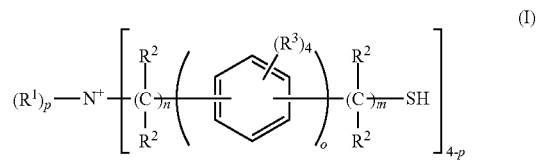

wherein
$R^1$ at each occurrence independently is hydrogen or a $C_{1-4}$-alkyl group,
$R^2$ at each occurrence independently is hydrogen, alkyl or aryl,
$R^3$ at each occurrence independently is hydrogen or alkyl or two vicinal groups $R^3$ together form an aromatic ring,
m is 1, 2, 3, 4, 5 or 6,
n is 1, 2, 3 or 4,
o is 1 or 2, and
p is 1, 2 or 3.

2. The strong-acid cation exchange resin of claim 1 wherein o is 1.

3. The strong-acid cation exchange resin of claim 1 wherein each group $R^1$ is methyl.

4. The strong-acid cation exchange resin of claim 1 wherein n is 1.

5. The strong-acid cation exchange resin of claim 1 wherein m is 2.

6. The strong-acid cation exchange resin of claim 1 wherein $R^2$ in each occurrence is hydrogen.

7. The strong-acid cation exchange resin of claim 1 wherein $R^3$ in each occurrence is hydrogen.

8. The strong-acid cation exchange resin of claim 1 wherein p is 2 or 3.

9. A process for partially neutralizing a strong-acid cation exchange resin comprising contacting a strong-acid ion exchange resin in acid form with a compound of formula II

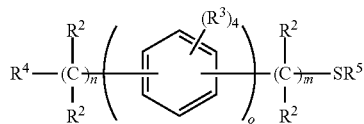

(II)

wherein
R² at each occurrence independently is hydrogen, alkyl or aryl,
R³ at each occurrence independently is hydrogen or alkyl or two vicinal groups R³ together form an aromatic ring,
R⁴ is $R^6$—C(O)—NH— or $(X^{z-})_{1/z}(R^1)_p(R^8)_{3-p}N^+$—
R⁵ is hydrogen or —C(O)—R⁷,
R¹ at each occurrence independently is hydrogen or a $C_{1-4}$-alkyl group,
R⁶ and R⁷ each independently are a $C_{1-4}$-alkyl group,
R⁸ is a group of formula III

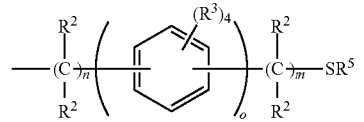

(III)

$X^{z-}$ is an anion,
m is 1, 2, 3, 4, 5 or 6,
n is 1, 2, 3 or 4,
o is 1 or 2,
p is 1, 2 or 3, and
z is 1, 2, 3 or 4.

10. The process of claim 9 wherein R⁴ is $(X^{z-})_{1/z}(R^1)_3N^+$—.

11. The process of claim 9 wherein R⁵ is —C(O)—R⁷.

12. The process of claim 9 for producing a strong-acid cation exchange resin of claim 1.

13. A process for producing a bisphenol wherein a phenolic compound is reacted with a carbonyl compound in the presence of a strong-acid cation exchange resin of claim 1 or in the presence of a strong-acid cation exchange resin produced according to the process of claim 9.

14. A process for isomerizing by-products resulting from the production of a bisphenol by reaction of a phenolic compound with a carbonyl compound wherein the by-products are contacted with a strong-acid cation exchange resin of claim 1 or with a strong-acid cation exchange resin produced according to the process of claim 9.

* * * * *